(12) United States Patent
Di Maiuta et al.

(10) Patent No.: US 10,046,998 B2
(45) Date of Patent: Aug. 14, 2018

(54) SURFACE-TREATED CALCIUM CARBONATE FOR BINDING AND BIOREMEDIATING HYDROCARBON-CONTAINING COMPOSITIONS

(75) Inventors: Nicola Di Maiuta, Zuchwil (CH); Patrick Schwarzentruber, Habsburg (CH); Michael Skovby, Meilen (CH)

(73) Assignee: Omya International AG, Oftringen (CH)

(*) Notice: Subject to any disclaimer, the term of this patent is extended or adjusted under 35 U.S.C. 154(b) by 570 days.

(21) Appl. No.: 14/232,012

(22) PCT Filed: Aug. 3, 2012

(86) PCT No.: PCT/EP2012/065251
§ 371 (c)(1),
(2), (4) Date: Feb. 27, 2014

(87) PCT Pub. No.: WO2013/020918
PCT Pub. Date: Feb. 14, 2013

(65) Prior Publication Data
US 2015/0034554 A1  Feb. 5, 2015

Related U.S. Application Data

(60) Provisional application No. 61/523,867, filed on Aug. 16, 2011.

(30) Foreign Application Priority Data

Aug. 9, 2011 (EP) .................................. 11177031

(51) Int. Cl.
| | | |
|---|---|---|
| *C02F 3/00* | (2006.01) |
| *C02F 3/34* | (2006.01) |
| *C09C 1/02* | (2006.01) |
| *C02F 1/28* | (2006.01) |
| *C02F 1/68* | (2006.01) |
| *C07C 53/126* | (2006.01) |
| *C12N 11/02* | (2006.01) |
| *C02F 101/32* | (2006.01) |
| *C02F 103/06* | (2006.01) |
| *C02F 103/08* | (2006.01) |
| *C02F 3/10* | (2006.01) |

(52) U.S. Cl.
CPC .............. *C02F 3/347* (2013.01); *C02F 1/281* (2013.01); *C02F 1/288* (2013.01); *C02F 1/681* (2013.01); *C02F 3/343* (2013.01); *C02F 3/344* (2013.01); *C07C 53/126* (2013.01); *C09C 1/021* (2013.01); *C12N 11/02* (2013.01); *C01P 2004/61* (2013.01); *C01P 2004/62* (2013.01); *C01P 2006/12* (2013.01); *C02F 3/103* (2013.01); *C02F 2101/32* (2013.01); *C02F 2103/06* (2013.01); *C02F 2103/08* (2013.01); *Y02W 10/15* (2015.05); *Y10T 428/2982* (2015.01)

(58) Field of Classification Search
CPC .......... C02F 3/347; C02F 3/343; C02F 3/344; C02F 3/341; C02F 3/322; C02F 3/1226; C02F 3/103; C02F 2103/08; C02F 2103/06; C02F 2103/32; C02F 2103/007; C02F 2103/36; C02F 1/52; C02F 1/5263; C02F 1/5272; C02F 1/681; C02F 1/288; C02F 1/281; C02F 3/00; C02F 3/34; C02F 3/348; C02F 1/28; B01J 2/003; B01J 2/30; B01J 2/006; B01D 17/02; B01D 17/0202; C01F 11/18; C01F 11/185; Y10T 428/2982; Y02W 10/15; C09C 1/021; C09C 1/024; C12N 11/02; C12N 1/14; C12N 1/20; C08K 9/12; C08K 9/08
USPC ......... 210/601, 620, 631, 690, 747.5, 747.7, 210/748.04, 749, 170.07, 170.09, 170.1, 210/170.11, 908, 691, 922, 924, 925; 405/128.1; 435/174, 177, 252.1, 254.1, 435/262, 262.5, 281; 423/419.1, 430; 428/403, 407
See application file for complete search history.

(56) References Cited

U.S. PATENT DOCUMENTS

| | | | |
|---|---|---|---|
| 4,151,136 A | 4/1979 | Cornell | |
| 5,415,777 A * | 5/1995 | Krempen | B09C 1/02 134/26 |
| 5,753,122 A | 5/1998 | Taylor et al. | |
| 5,780,290 A * | 7/1998 | Rosenberg | A62D 3/02 210/601 |
| 6,057,147 A | 5/2000 | Overland et al. | |
| 2002/0022084 A1 | 2/2002 | Calhoun et al. | |
| 2006/0032820 A1 | 2/2006 | Reddy | |
| 2008/0020947 A1 | 1/2008 | Park et al. | |
| 2010/0069552 A1 | 3/2010 | Guerret et al. | |

(Continued)

FOREIGN PATENT DOCUMENTS

| | | | |
|---|---|---|---|
| EP | 0594125 A2 | 4/1994 |
| EP | 0617991 A1 | 5/1994 |

(Continued)

OTHER PUBLICATIONS

The International Search Report dated Sep. 20, 2012 for PCT Application No. PCT/EP2012/065251.

(Continued)

*Primary Examiner* — Claire A Norris
*Assistant Examiner* — Julia L. Wun
(74) *Attorney, Agent, or Firm* — Amster, Rothstein & Ebenstein LLP

(57) ABSTRACT

The invention relates to a surface-treated calcium carbonate for binding and bioremediating hydrocarbon-containing compositions, to a method for binding and bioremediating hydrocarbon-containing compositions as well as to the use of surface-treated calcium carbonate for binding and bioremediating hydrocarbon-containing compositions and to a composite material comprising the surface-treated calcium carbonate and a hydrocarbon-containing composition.

34 Claims, No Drawings

(56) References Cited

U.S. PATENT DOCUMENTS

2010/0133195 A1* 6/2010 Gane ................. B01J 20/043
  210/667
2010/0147780 A1* 6/2010 Endo ................. G01N 1/4077
  210/768

FOREIGN PATENT DOCUMENTS

| EP | 0962492 A1 | 8/1999 |
| EP | 2264108 A1 | 12/2010 |
| EP | 2264109 A1 | 12/2012 |
| GB | 1192063 | 5/1970 |
| GB | 1353945 | 5/1974 |
| GB | 1400256 | 7/1975 |
| WO | 0039222 A1 | 7/2000 |
| WO | 2004083316 A1 | 9/2004 |
| WO | 2005121257 A2 | 12/2005 |
| WO | 2007093993 A2 | 8/2007 |
| WO | 2008015688 A2 | 2/2008 |
| WO | 2009074492 A1 | 6/2009 |
| WO | 2010080266 A2 | 7/2010 |
| WO | 2010112696 A1 | 10/2010 |
| WO | 2011060107 A1 | 5/2011 |

OTHER PUBLICATIONS

The Written Opinion of the International Searching Authority dated Sep. 20, 2012 for PCT Application No. PCT/EP2012/065251.

* cited by examiner

SURFACE-TREATED CALCIUM CARBONATE FOR BINDING AND BIOREMEDIATING HYDROCARBON-CONTAINING COMPOSITIONS

CROSS-REFERENCE TO RELATED APPLICATIONS

This application is a U.S. national phase of PCT Application No. PCT/EP2012/065251, filed Aug. 3, 2012, which claims priority to European Application No. 11177031.9, filed Aug. 9, 2011 and U.S. Provisional Application No. 61/523,867, filed Aug. 16, 2011.

The invention relates to a surface-treated calcium carbonate for binding and bioremediating hydrocarbon-containing compositions, to a method for binding and bioremediating hydrocarbon-containing compositions as well as to the use of surface-treated calcium carbonate for binding and bioremediating hydrocarbon-containing compositions and to a composite material comprising the surface-treated calcium carbonate and a hydrocarbon-containing composition.

Pollution of soils, sea water or ground water with water-insoluble fluids such as compositions comprising hydrocarbons has posed a serious environmental problem all over the world. In this regard, hydrocarbon-containing compositions such as crude oil contribute significantly to the contamination of sea water and soils, while refined petroleum products such as gasoline, aviation fuel, diesel fuel and other refined petroleum products are the most frequent pollutants of ground water and soils. In particular, oil spills including releases of crude oil from tankers, offshore platforms, drilling rigs and wells, as well as spills of refined petroleum products and heavier fuels used by large ships such as bunker fuel, or the spill of oily refuse or waste oil have become an increasing problem.

In the art, several approaches for the remediation of hydrocarbon-polluted media such as soils, ground water, sea water and shore lines have been proposed. For instance, in the case of hydrocarbon-polluted water one approach involves the addition of sinking agents in the form of emulsifying agents and dispersants in order to bind water-insoluble fluids such as crude oil and to keep the mixture of sinking agent and crude oil suspended in the sea water. For example, GB 1 353 945 relates to a method for converting a petroleum product into a biodegradable emulsion which comprises bringing the petroleum product into contact with water and an emulsifying composition comprising: a) from 15 to 80 parts by weight of a micro-organism nutrient comprising molasses, cellulose, a sugar beet waste, casein, a malt extract, a proteose, an ammonium salt, an amine, an amide and/or vinasse, b) from 10 to 50 parts by weight of a surface tension reducing component which is an alkali or alkaline earth metal salt and comprises calcium silicate, sodium silicate, potassium silicate, calcium carbonate, sodium carbonate, potassium carbonate, ammonium carbonate, dibasic sodium phosphate, dicalcium phosphate, and/or a mono- or dibasic ammonium phosphate, and c) a diluent, and mixing the components to form an emulsion. EP 0 617 991 A1 refers to a method of recovering oil from waste oil fluids and of removal of oil from industrial wastewaters, respectively, using water-soluble polymers dispersed in a concentrated salt media. US 2006/032820 A1 describes a process for removing oil from a solid wellbore material such as drill cuttings or water such as produced by a subterranean formation include contacting the solid material/water with an amino-substituted polymer such as chitosan and a halogenating agent. GB 1,192,063 relates to a method of treating water polluted on its surface with oil or oil derivatives which comprises applying to the oil or oil derivatives a mineral powder which has been treated to render it hydrophobic or more hydrophobic, whereby an agglomerate of the powder and the oil or oil derivatives, having a specific gravity greater than that of the water, is formed and sinks through the water.

In a medium such as sea water, this approach has the advantage that the oil, e.g. from an oil spill, is relatively quickly removed from the water surface by suspending the mixture of sinking agent and oil in the water and prevents, thus, a hydrocarbon pollution of adjacent shore lines to a great extent.

However, this approach often causes problems because the suspended mixture comprising the respective sinking agent and oil is considered as being toxic for several marine organisms with consequent higher mortality rates for e.g. sea birds, marine mammals and fishes and a consequent disturbance of the ecological balance of the marine environment for several years. Furthermore, the suspension of the mixture of sinking agent and oil in the sea water allows it's easier distribution over a wide area by the ocean current and, thus, the disadvantageous effects can still be observed in distant areas.

Another approach considers the utilization of microorganisms such as bacteria and algae effective in biodegrading petroleum and petroleum products by inoculating the polluted medium with the respective microorganisms. For example, U.S. Pat. No. 5,753,122 relates to an in situ thermally enhanced microbial remediation method for cleaning-up toxic components of petroleum fuel hydrogens and halogenated organic solvents. WO 2010/080266 A2 relates to a strain of *Gordonia sihwensis* that may be used to sequester and/or biodegrade hydrocarbons. WO 2011/060107 A1 refers to algae-based bioremediation systems and methods in which algae is grown in a photobioreactor with nutrients supplied from a nutrient system. EP 0 962 492 A1 relates to a composition for use in the bioremediation of soil or fluids contaminated by organic compounds, comprising chitin and/or derivatives thereof and microorganisms. WO 2007/093993 A2 relates in general to the field of hydrocarbon degradation, and more particularly, to environmentally safe bacterial compositions useful for cleaning and treating hydrocarbon-contaminated water and surfaces. U.S. Pat. No. 6,057,147 directed to an apparatus and method for enhanced bioremediation of hydrocarbons removed from a contaminated object comprising: (a) a basin for cleansing said hydrocarbon-contaminated object, said basin having a means for introducing a recycling bioremediating cleaning solution (NATURES WAY PC™) for washing said object, a means for draining said solution from said basin into a biochamber reservoir and a means for screening particles from said solution upon entry into said reservoir; and (b) said reservoir having a means for temperature control between 90° to 112° F., means for aerating said solution, means for agitating said solution, an outlet means to a plurality of filters for filtering said solution, an inlet means from said filters and means for removing filtered sediments. WO 2008/015688 A2 refers to a bio-assisted method for treatment of hydrocarbon contaminated soil employing novel microbes which are capable of decontaminating hydrocarbon contaminated soil having free flowing water or in slurry form or having large amount of gravels. US 2008/020947 A1 discloses microorganisms having excellent biodegradability and a method for the bioremediation of oil-contaminated soil. WO 2010/112696 A1 relates to *Rho-*

*dococcus wratislaviensis* CNCM 1-4088 bacteria, or *Rhodococcus aetherivorans* CNCM 1-4089 bacteria, capable of degrading multiple petroleum compounds in solution in aqueous effluents. EP 0594125 A2 refers to a carrier for supporting microorganisms is characterized by supporting the microorganisms for use in soil remediation, having pores, and holding a nutrient in the pores or being a nutrient for the microorganisms. EP 0962492 relates to the use of chitin and/or derivatives thereof as biocatalysts or biostimulators to stimulate, accelerate, enhance and protect the growth of microorganism and a method for the bioremediation of soils and fluids contaminated by organic compounds, comprising the addition of chitin and/or derivatives thereof to said soils and fluids However, the activity of most of the bacteria capable of biodegrading hydrocarbon products is best if temperatures and concentrations of inorganic nutrients are in specific optimal ranges. Thus, under real conditions such as at varying temperatures and limited nutrients the obtained action of such bacteria is in some cases insufficient to obtain an optimal bioremediation of hydrocarbon-polluted media such as soils, sea water, ground water and/or other polluted media.

Therefore, there is a continuous need for alternative materials and methods for binding and bioremediating hydrocarbon-containing compositions, which provide a better performance than existing materials and methods and effectively decrease the concentration of hydrocarbon-containing compositions in sea water, ground water, soils and other media to be treated.

This and other objects are solved by the subject-matter of the present invention. According to a first aspect of the present invention, a surface-treated calcium carbonate for binding and bioremediating hydrocarbon-containing compositions having a degradation rate for the hydrocarbon-containing composition of at least 25%, based on the total weight of the hydrocarbon-containing composition is provided, wherein at least 10% of the aliphatic carboxylic acid accessible surface area of the calcium carbonate is covered by a coating comprising at least one aliphatic carboxylic acid having between 5 and 24 carbon atoms and/or reaction products thereof.

The inventors surprisingly found that the foregoing product according to the present invention provides an efficient binding and bioremediating activity for hydrocarbon-containing compositions and leads thus to a hydrocarbon-polluted medium containing an amount of hydrocarbons that is at least 25% lower than the amount of hydrocarbons in a corresponding hydrocarbon-polluted medium obtained by the same method but without contacting it with the surface-treated calcium carbonate. More precisely, the inventors found that the binding and bioremediating activity for hydrocarbon-containing compositions can be improved by a calcium carbonate that is surface-treated with defined aliphatic carboxylic acids.

It should be understood that for the purposes of the present invention, the following terms have the following meaning:

The term "calcium carbonate" in the meaning of the present invention refers to ground or natural calcium carbonate (GCC), and/or synthetic or precipitated calcium carbonate (PCC) and/or surface modified calcium carbonate (MCC). "Ground calcium carbonate" (GCC) in the meaning of the present invention is a calcium carbonate obtained from natural sources, such as limestone, marble or chalk or dolomite, and processed through a treatment such as grinding, screening and/or fractionizing by a wet and/or dry process, for example, by means of a cyclone or classifier. "Precipitated calcium carbonate" (PCC) in the meaning of the present invention is a synthesized material, generally obtained by precipitation following reaction of carbon dioxide and lime in an aqueous environment or by precipitation of a calcium and carbonate ion source in water. "Surface-modified calcium carbonate" (MCC) in the meaning of the present invention refers to a natural calcium carbonate and/or precipitated calcium carbonate obtained by reacting it with an acid and with carbon dioxide prior to the preparation of the surface-treated calcium carbonate, wherein the carbon dioxide is formed in situ by the acid treatment and/or is supplied from an external source.

The term "surface-treated" calcium carbonate in the meaning of the present invention refers to a ground calcium carbonate and/or precipitated calcium carbonate and/or surface-modified calcium carbonate that has been processed with aliphatic carboxylic acids through an additional treatment step in order to render the surface of the calcium carbonate particles more hydrophobic.

The term "aliphatic carboxylic acid" in the meaning of the present invention refers to straight chain, branched chain, saturated, unsaturated or alicyclic organic compounds composed of carbon and hydrogen. Said organic compound further contains a carboxyl group placed at the end of the carbon skeleton.

The term "aliphatic carboxylic acid accessible surface area" in the meaning of the present invention refers to the surface of the calcium carbonate particle that is accessible or exposed to the aliphatic carboxylic acid applied by coating techniques known to the skilled person such as hot fluidised bed spray coating, hot-wet coating, solvent-assisted or self-assembly coating and the like and thereby forming a monolayer of aliphatic carboxylic acid on the surface of the calcium carbonate particle. In this regard, it should be noted that the amount of aliphatic carboxylic acid required for full saturation of the accessible surface area is defined as a monolayer concentration. Higher concentrations thus can be chosen as well thereby forming bilayered or multi-layered structures on the surface of the calcium carbonate particle. Such monolayer concentrations can be readily calculated by the skilled person, based on the publication of Papirer, Schultz and Turchi (Eur. Polym. J., Vol. 20, No. 12, pp. 1155-1158, 1984).

The term "reaction products" in the meaning of the present invention refers to the products typically obtained by contacting a ground calcium carbonate and/or a precipitated calcium carbonate with an aliphatic carboxylic acid having between 5 and 24 carbon atoms. Said reaction products are preferably formed between the applied aliphatic carboxylic acid and molecules located at the surface of the ground calcium carbonate and/or the precipitated calcium carbonate.

The term "hydrocarbon-containing composition" in the meaning of the present invention refers to a composition comprising at least one type of hydrocarbons. The term "hydrocarbon", as used herein, refers to straight chain, branched chain, saturated, unsaturated or alicyclic organic compounds composed of carbon and hydrogen. They include the alkanes, alkenes, alkynes and aromatic hydrocarbons.

The term "bioremediating" or "bioremediation" in the meaning of the present invention refers to the at least partially removal of pollutants by using microorganisms.

The term "degradation rate" in the meaning of the present invention corresponds to the reduction of the amount of hydrocarbons in the hydrocarbon-containing composition within 60 days by the addition of the inventive surface-treated calcium carbonate in comparison to a corresponding hydrocarbon-containing composition containing no surface-treated calcium carbonate.

Another aspect of the present invention is directed to a method for binding and bioremediating hydrocarbon-containing compositions, comprising the following steps:
a) providing a hydrocarbon-containing composition;
b) providing the at least one surface-treated calcium carbonate; and
c) contacting the hydrocarbon-containing composition of step a) with the surface-treated calcium carbonate of step b) for obtaining a composite material comprising said surface-treated calcium carbonate and said hydrocarbon-containing composition.

It is preferred that the hydrocarbon-containing composition is crude oil and/or a refined petroleum product selected from the group comprising gasoline, diesel fuel, aviation fuel, hydraulic oil, kerosene and mixtures thereof. It is further preferred that step c) is carried out by at least partially covering the surface of the hydrocarbon-containing composition of step a) with the surface-treated calcium carbonate of step b) and/or mixing the hydrocarbon-containing composition of step a) with the surface-treated calcium carbonate of step b). It is also preferred that step c) is carried out in that the weight ratio of hydrocarbon-containing composition and surface-treated calcium carbonate is from 10:1 to 1:100, more preferably from 1:1 to 1:50, even more preferably from 1:1 to 1:25 and most preferably from 1:1 to 1:15. It is even further preferred that the method further comprises step d) of contacting the composite material obtained in step c) with a composition comprising at least one microorganism capable of degrading at least one component of the hydrocarbon-containing composition. It is further preferred that the at least one microorganism capable of degrading at least one component of the hydrocarbon-containing composition is selected from at least one strain of bacteria and/or fungi. It is preferred that the at least one strain of bacteria is selected from the group comprising *Psychrobacter, Pseudomonas, Pseudobacterium, Acinetobacter, Vibrio, Planococcus, Actinobacterium, Arthrobacter, Marinobacter, Methylosinus, Methylomonas, Methylobacterium, Mycobacterium, Nocardia, Bacillus, Brevibacterium, Micrococcus, Corynebacterium, Sarcina, Streptomyces, Flavobacterium, Xanthomonas* and mixtures thereof, more preferably is selected from the group comprising *Psychrobacter glacincola, Acinetobacter calcoaceticus, Acinetobacter faecalis* and mixtures thereof. It is still further preferred that step c) and step d) are carried out simultaneously or separately. It is also preferred that step c) and/or step d) are repeated one or more times.

A further aspect of the present invention is directed to the use of the surface-treated calcium carbonate for binding and bioremediating hydrocarbon-containing compositions. It is preferred that the surface-treated calcium carbonate is used in soil, sea water, ground water, flat water, shore lines, containers and/or reservoirs.

A still further aspect of the present invention is directed to a composite material comprising the surface-treated calcium carbonate and a hydrocarbon-containing composition.

When in the following reference is made to preferred embodiments or technical details of the inventive surface-treated calcium carbonate for binding and bioremediating hydrocarbon-containing compositions, it is to be understood that these preferred embodiments or technical details also refer to the inventive method for binding and bioremediating hydrocarbon-containing compositions, the inventive use of the surface-treated calcium carbonate as well as to the composite material comprising the surface-treated calcium carbonate and the hydrocarbon-composition defined herein and vice versa (as far as applicable). If, for example, it is set out that the inventive surface-treated calcium carbonate preferably comprises ground calcium carbonate and/or precipitated calcium carbonate and/or surface-modified calcium carbonate, also the surface-treated calcium carbonate provided in the inventive method, the inventive use as well as the inventive composite material preferably comprise ground calcium carbonate and/or precipitated calcium carbonate and/or surface-modified calcium carbonate.

According to one preferred embodiment of the inventive surface-treated calcium carbonate, the surface-treated calcium carbonate comprises ground calcium carbonate and/or precipitated calcium carbonate and/or surface-modified calcium carbonate, preferably ground calcium carbonate.

According to another preferred embodiment of the inventive surface-treated calcium carbonate, the source of ground calcium carbonate (GCC) is selected from marble, chalk, calcite, dolomite, limestone and mixtures thereof and/or the precipitated calcium carbonate (PCC) is selected from one or more of the aragonitic, vateritic and calcitic mineralogical crystal forms.

According to yet another preferred embodiment of the inventive surface-treated calcium carbonate, the surface-treated calcium carbonate has a weight median particle diameter $d_{50}$ value of between 0.1 µm and 250 µm, preferably between 1 µm and 200 µm, more preferably between 1 µm and 150 µm, even more preferably between 1 µm and 100 µm and most preferably between 3 µm and 100 µm.

According to one preferred embodiment of the inventive surface-treated calcium carbonate, the coating of the surface-treated calcium carbonate comprises at least one aliphatic carboxylic acid selected from the group consisting of pentanoic acid, hexanoic acid, heptanoic acid, octanoic acid, nonanoic acid, decanoic acid, undecanoic acid, lauric acid, tridecanoic acid, myristic acid, pentadecanoic acid, palmitic acid, heptadecanoic acid, stearic acid, nonadecanoic acid, arachidic acid, heneicosylic acid, behenic acid, tricosylic acid, lignoceric acid and mixtures thereof, preferably the aliphatic carboxylic acid is selected from the group consisting of octanoic acid, decanoic acid, lauric acid, myristic acid, palmitic acid, stearic acid, arachidic acid and mixtures thereof and most preferably the aliphatic carboxylic acid is selected from the group consisting of myristic acid, palmitic acid, stearic acid and mixtures thereof.

According to another preferred embodiment of the inventive surface-treated calcium carbonate, at least 20% of the aliphatic carboxylic acid accessible surface area of the calcium carbonate is covered by a coating comprising at least one aliphatic carboxylic acid and/or reaction products thereof, preferably at least 30% of the accessible surface area and most preferably at least 50% of the accessible surface area.

According to yet another preferred embodiment of the inventive surface-treated calcium carbonate, the surface-treated calcium carbonate further comprises at least one microorganism capable of degrading at least one component of the hydrocarbon-containing composition.

According to one preferred embodiment of the inventive surface-treated calcium carbonate, the surface-treated calcium carbonate is immobilized with at least one microorganism capable of degrading at least one component of the hydrocarbon-containing composition.

According to another preferred embodiment of the inventive surface-treated calcium carbonate, the at least one microorganism capable of degrading at least one component of the hydrocarbon-containing composition is selected from at least one strain of bacteria and/or fungi.

According to yet another preferred embodiment of the inventive surface-treated calcium carbonate, the at least one strain of bacteria and/or fungi is at least one strain of petroleum-degrading bacteria and/or petroleum-degrading fungi.

According to one preferred embodiment of the inventive surface-treated calcium carbonate, the at least one strain of bacteria is selected from the group comprising *Psychrobacter, Pseudomonas, Pseudobacterium, Acinetobacter, Vibrio, Planococcus, Actinobacterium, Arthrobacter, Marinobacter, Methylosinus, Methylomonas, Methylobacterium, Mycobacterium, Nocardia, Bacillus, Brevibacterium, Micrococcus, Corynebacterium, Sarcina, Streptomyces, Flavobacterium, Xanthomonas* and mixtures thereof, more preferably is selected from the group comprising *Psychrobacter glacincola, Acinetobacter calcoaceticus, Acinetobacter faecalis* and mixtures thereof.

According to another preferred embodiment of the inventive surface-treated calcium carbonate, the surface-treated calcium carbonate is in powder form and/or in the form of granules or in the form of slurry.

According to yet another preferred embodiment of the inventive surface-treated calcium carbonate, the surface-treated calcium carbonate is incorporated in a nonwoven fabric. It is preferred that the surface-treated calcium carbonate is incorporated in a biodegradable nonwoven fabric.

In the following, it is referred to further preferred embodiments of the present invention:

In accordance with the inventive surface-treated calcium carbonate, at least 10% of the aliphatic carboxylic acid accessible surface area of the calcium carbonate is covered by a coating comprising at least one aliphatic carboxylic acid having between 5 and 24 carbon atoms and/or reaction products thereof.

In one preferred embodiment, the surface-treated calcium carbonate comprises ground (or natural) calcium carbonate (GCC) or precipitated (or synthetic) calcium carbonate (PCC) or surface-modified calcium carbonate (MCC). In another preferred embodiment, the surface-treated calcium carbonate comprises a mixture of at least two calcium carbonates selected from GCC, PCC and MCC. For example, the surface-treated calcium carbonate comprises a mixture of GCC and PCC. Alternatively, the surface-treated calcium carbonate comprises a mixture of GCC and MCC. Alternatively, the surface-treated calcium carbonate comprises a mixture of PCC and MCC.

In one especially preferred embodiment, the surface-treated calcium carbonate comprises ground calcium carbonate.

Ground (or natural) calcium carbonate (GCC) is understood to be a naturally occurring form of calcium carbonate, mined from sedimentary rocks such as limestone or chalk, or from metamorphic marble rocks. Calcium carbonate is known to exist as three types of crystal polymorphs: calcite, aragonite and vaterite. Calcite, the most common crystal polymorph, is considered to be the most stable crystal form of calcium carbonate. Less common is aragonite, which has a discrete or clustered needle orthorhombic crystal structure. Vaterite is the rarest calcium carbonate polymorph and is generally unstable. Ground calcium carbonate is almost exclusively of the calcitic polymorph, which is said to be trigonal-rhombohedral and represents the most stable of the calcium carbonate polymorphs.

Preferably, the source of the ground calcium carbonate is selected from the group comprising marble, chalk, calcite, dolomite, limestone and mixtures thereof. In a preferred embodiment, the source of the ground calcium carbonate is calcite.

The term "source" of the calcium carbonate in the meaning of the present invention refers to the naturally occurring mineral material from which the calcium carbonate is obtained. The source of the calcium carbonate may comprise further naturally occurring components such as magnesium carbonate, alumino silicate etc.

Additionally or alternatively, the surface-treated calcium carbonate comprises a precipitated calcium carbonate (PCC). Calcium carbonate polymorphs of the PCC type often include, in addition to calcites, less stable polymorphs of the aragonitic-type, which has an orthorhombic, acicular crystal shape, and hexagonal vateritic-type, which has an even lower stability than aragonite. The different PCC forms may be identified according to their characteristic x-ray powder diffraction (XRD) peaks. PCC synthesis most commonly occurs by a synthetic precipitation reaction that includes a step of contacting carbon dioxide with a solution of calcium hydroxide, the latter being most often provided on forming an aqueous suspension of calcium oxide, also known as burnt lime, and the suspension of which is commonly known as milk of lime. Depending on the reaction conditions, this PCC can appear in various forms, including both stable and unstable polymorphs. Indeed, PCC often represents a thermodynamically unstable calcium carbonate material. When referred to in the context of the present invention, PCC shall be understood to mean synthetic calcium carbonate products obtained notably by carbonation of a slurry of calcium hydroxide, commonly referred to in the art as a slurry of lime or milk of lime when derived from finely divided calcium oxide particles in water.

Preferred precipitated calcium carbonate is selected from aragonitic, vateritic or calcitic mineralogical crystal forms or mixtures thereof.

Additionally or alternatively, said GCC or PCC may be surface reacted to form a surface-modified calcium carbonate, which is a material comprising GCC and/or PCC and an insoluble, at least partially crystalline, non-carbonate calcium salt extending from the surface of at least part of the calcium carbonate. Such surface-modified products may, for example, be prepared according to WO 00/39222, WO 2004/083316, WO 2005/121257, WO 2009/074492, EP 2 264 108 A1, EP 2 264 109 A1.

For example, the surface-modified calcium carbonate is obtained by reacting a natural calcium carbonate and/or precipitated calcium carbonate with an acid and with carbon dioxide prior to the preparation of the surface-treated calcium carbonate, wherein the carbon dioxide is formed in situ by the acid treatment and/or is supplied from an external source. The acid treatment can be carried out with an acid having a $pK_a$ at 25° C. of 2.5 or less. If the $pK_a$ at 25° C. is 0 or less, the acid is preferably selected from sulphuric acid, hydrochloric acid, or mixtures thereof. If the $pK_a$ at 25° C. is from 0 to 2.5, the acid is preferably selected from $H_2SO_3$, $M^+HSO_4^-$ ($M^+$ is an alkali metal ion selected from the group comprising sodium and potassium), $H_3PO_4$, oxalic acid or mixtures thereof.

In an especially preferred embodiment, the calcium carbonate particles of the present surface-treated calcium carbonate have a weight median particle diameter $d_{50}$ value of from 0.1 μm to 250 μm before surface treatment, preferably from 1 μm to 200 μm, more preferably from 1 μm to 150 μm and most preferably from 1 μm to 100 μm, measured according to the sedimentation method. In one especially preferred embodiment, the calcium carbonate particles of the present surface-treated calcium carbonate have a weight median particle diameter $d_{50}$ value of from 3 μm to 100 μm before surface treatment. For example, the calcium carbonate particles of the surface-treated calcium carbonate have a weight median particle diameter $d_{50}$ value of 19.5 μm before surface treatment. Alternatively, the calcium carbonate particles of the surface-treated calcium carbonate have a weight median particle diameter $d_{50}$ value of 1.4 μm before surface treatment. Calcium carbonate particles having a $d_{98}$ of less than 100 microns, preferably of less than 85 microns may also be advantageous, for example 83 microns. Alternatively, calcium carbonate particles having a $d_{98}$ of less than 20 microns, preferably of less than 10 microns may be advantageous, for example 5 microns.

As used herein and as generally defined in the art, the weight median particle diameter "$d_{98}$" value is defined as the size at which 98% (the mean point) of the particle volume or mass is accounted for by particles having a diameter equal to the specified value. The weight median particle diameter was measured according to the sedimentation method. The sedimentation method is an analysis of sedimentation behaviour in a gravimetric field. The measurement is made with a Sedigraph™ 5100 of Micromeritics Instrument Corporation.

The calcium carbonate particles of the present surface-treated calcium carbonate preferably have a specific surface area of from 0.5 m$^2$/g to 120 m$^2$/g before surface treatment, preferably 0.5 m$^2$/g to 100 m$^2$/g, more preferably 0.5 m$^2$/g to 75 m$^2$/g and most preferably 0.5 m$^2$/g to 50 m$^2$/g, measured using nitrogen and the BET method. For example, the calcium carbonate particles of the surface-treated calcium carbonate have a specific surface area of from 0.5 m$^2$/g to 10 m$^2$/g before surface treatment. Alternatively, the calcium carbonate particles of the present surface-treated calcium carbonate have a specific surface area of from 5 m$^2$/g to 15 m$^2$/g.

In one preferred embodiment, the calcium carbonate particles of the present surface-treated calcium carbonate have a specific surface area within the range of 0.5 m$^2$/g to 120 m$^2$/g and a weight median particle diameter $d_{50}$ value within the range of 0.1 to 250 μm before surface treatment. More preferably, the specific surface area is within the range of 0.5 m$^2$/g to 100 m$^2$/g and the weight median particle diameter $d_{50}$ value is within the range of 1 to 200 μm before surface treatment. Even more preferably, the specific surface area is within the range of 0.5 m$^2$/g to 75 m$^2$/g and the weight median particle diameter is within the range of 1 to 150 μm before surface treatment. Most preferably, the specific surface area is within the range of 0.5 m$^2$/g to 50 m$^2$/g and the weight median particle diameter $d_{50}$ value is within the range of 1 to 100 μm before surface treatment. For example, the calcium carbonate particles of the present surface-treated calcium carbonate have a specific surface area within the range of 5 m$^2$/g to 15 m$^2$/g and a weight median particle diameter $d_{50}$ value of 1.4 μm. Alternatively, the calcium carbonate particles of the present surface-treated calcium carbonate have a specific surface area within the range of 0.5 m$^2$/g to 10 m$^2$/g and a weight median particle diameter $d_{50}$ value of 19.5 μm.

In accordance with the inventive surface-treated calcium carbonate, at least 10% of the aliphatic carboxylic acid accessible surface area of the calcium carbonate is covered by a coating comprising at least one aliphatic carboxylic acid having between 5 and 24 carbon atoms and/or reaction products thereof.

In this regard, the at least one aliphatic carboxylic acid may be selected from one or more straight chain, branched chain, saturated, unsaturated and/or alicyclic carboxylic acids. Preferably, the aliphatic carboxylic acid is a monocarboxylic acid, i.e. the aliphatic carboxylic acid is characterized in that a single carboxyl group is present. Said carboxyl group is placed at the end of the carbon skeleton.

In one preferred embodiment, the at least one aliphatic carboxylic acid is selected from saturated unbranched carboxylic acids, i.e. the at least one aliphatic carboxylic acid is selected from the group consisting of pentanoic acid, hexanoic acid, heptanoic acid, octanoic acid, nonanoic acid, decanoic acid, undecanoic acid, lauric acid, tridecanoic acid, myristic acid, pentadecanoic acid, palmitic acid, heptadecanoic acid, stearic acid, nonadecanoic acid, arachidic acid, heneicosylic acid, behenic acid, tricosylic acid, lignoceric acid and mixtures thereof.

In a further preferred embodiment, the at least one aliphatic carboxylic acid is selected from the group consisting of octanoic acid, decanoic acid, lauric acid, myristic acid, palmitic acid, stearic acid, arachidic acid and mixtures thereof. Preferably, the at least one aliphatic carboxylic acid is selected from the group consisting of myristic acid, palmitic acid, stearic acid and mixtures thereof.

In an especially preferred embodiment, the aliphatic carboxylic acid is stearic acid.

In one preferred embodiment, the aliphatic carboxylic acid comprises a mixture of at least two aliphatic carboxylic acids having between 5 and 24 carbon atoms. Preferably, if the aliphatic carboxylic acid comprises a mixture of at least two aliphatic carboxylic acids having between 5 and 24 carbon atoms, one aliphatic carboxylic acid is stearic acid.

In a further preferred embodiment, the aliphatic carboxylic acid comprises a mixture of two aliphatic carboxylic acids having between 5 and 24 carbon atoms, wherein one aliphatic carboxylic acid is stearic acid and the other one is selected from the group consisting of octanoic acid, myristic acid, palmitic acid, arachidic acid, behenic acid and lignoceric acid.

If the aliphatic carboxylic acid comprises a mixture of two aliphatic carboxylic acids having between 5 and 24 carbon atoms, the mole ratio of stearic acid and the second aliphatic carboxylic acid is from 99:1 to 1:99, more preferably from 50:1 to 1:50, even more preferably from 25:1 to 1:25 and most preferably from 10:1 to 1:10. In one especially preferred embodiment of the present invention, the mole ratio of stearic acid and the second aliphatic carboxylic acid is from 90:1 to 1:1, more preferably from 90:1 to 10:1 and most preferably from 90:1 to 50:1. In another preferred embodiment, the mole ratio of stearic acid and the second aliphatic carboxylic acid is 1:1.

If the aliphatic carboxylic acid comprises a mixture of two aliphatic carboxylic acids having between 5 and 24 carbon atoms, at least 10% of the aliphatic carboxylic acid accessible surface area of the calcium carbonate is covered by a coating preferably comprising a mixture of stearic acid, myristic acid and/or reaction products thereof. In a further preferred embodiment, at least 10% of the aliphatic carboxylic acid accessible surface area of the calcium carbonate is covered by a coating comprising a mixture of stearic acid, palmitic acid and/or reaction products thereof. In yet another preferred embodiment, at least 10% of the aliphatic carboxylic acid accessible surface area of the calcium carbonate is covered by a coating comprising a mixture of stearic acid, arachidic acid and/or reaction products thereof. In still another preferred embodiment, at least 10% of the aliphatic carboxylic acid accessible surface area of the calcium carbonate is covered by a coating comprising a mixture of stearic acid, behenic acid and/or reaction products thereof. In a further preferred embodiment, at least 10% of the aliphatic carboxylic acid accessible surface area of the calcium carbonate is covered by a coating comprising a mixture of stearic acid, lignoceric acid and/or reaction products thereof. In yet another preferred embodiment, at least 10% of the aliphatic carboxylic acid accessible surface area of the calcium carbonate is covered by a coating comprising a mixture of stearic acid, octanoic acid and/or reaction products thereof.

The at least one aliphatic carboxylic acid is preferably present in the coating covering the calcium carbonate in a quantity such that the total weight of said at least one aliphatic carboxylic acid and/or reaction products of said at least one aliphatic carboxylic acid on the surface of the surface-treated calcium carbonate product is between 0.01% w/w and 50% w/w of the calcium carbonate.

In one preferred embodiment, the at least one aliphatic carboxylic acid is present in the coating covering the calcium carbonate in a quantity such that the total weight of said at least one aliphatic carboxylic acid and/or reaction products of said at least one aliphatic carboxylic acid on the surface of the surface-treated calcium carbonate product is less than 50% w/w, more preferably less than 15% w/w and most preferably less than 10% w/w of the calcium carbonate.

In another preferred embodiment, the at least one aliphatic carboxylic acid and/or reaction products of said at least one aliphatic carboxylic acid are present in the coating covering at least 10% of the aliphatic carboxylic acid accessible surface area of the calcium carbonate in an amount of about 0.1 wt.-% to 10 wt.-%, more preferably of about 0.1 wt.-% to 8 wt.-%, even more preferably of about 0.2 wt.-% to 5 wt.-% and most preferably of about 0.2 wt.-% to 2.5 wt.-%, based on the dry weight of the calcium carbonate.

Alternatively, at least 20% of the aliphatic carboxylic acid accessible surface area of the calcium carbonate particles is covered by a coating comprising the at least one aliphatic carboxylic acid and/or reaction products of said at least one aliphatic carboxylic acid. In a preferred embodiment, at least 30% of the aliphatic carboxylic acid accessible surface area of the calcium carbonate particles is covered by a coating comprising the at least one aliphatic carboxylic acid and/or reaction products of said at least one aliphatic carboxylic acid, preferably at least 50% of the aliphatic carboxylic acid accessible surface area. In another preferred embodiment, at least 75% of the aliphatic carboxylic acid accessible surface area of the calcium carbonate particles is covered by a coating comprising the at least one aliphatic carboxylic acid and/or reaction products of said at least one aliphatic carboxylic acid. For example, at least 90% of the aliphatic carboxylic acid accessible surface area of the calcium carbonate particles is covered by a coating comprising the at least one aliphatic carboxylic acid and/or reaction products of said at least one aliphatic carboxylic acid. Alternatively, between 10% and 25% of the aliphatic carboxylic acid accessible surface area of the calcium carbonate particles is covered by a coating comprising the at least one aliphatic carboxylic acid and/or reaction products of said at least one aliphatic carboxylic acid.

In one preferred embodiment, at least 75% of the aliphatic carboxylic acid accessible surface area of the calcium carbonate particles is covered by a coating comprising stearic acid and/or reaction products of stearic acid.

In another preferred embodiment, between 10% and 25% of the aliphatic carboxylic acid accessible surface area of the calcium carbonate particles is covered by a coating comprising stearic acid and/or reaction products of stearic acid.

In one preferred embodiment, the at least one aliphatic carboxylic acid has a solubility in water of below 5 g/100 ml of water, preferably of below 2.5 g/100 ml of water, even more preferably of below 1 g/100 ml of water and most preferably of below 0.5 g/100 ml of water. In one especially preferred embodiment, the at least one aliphatic carboxylic acid is immiscible in water.

The surface-treated calcium carbonate is preferably in the form of a particulate material, and may have a particle size distribution as conventionally employed for the material(s) involved in the treatment of hydrocarbon-polluted media. In general, the weight median particle diameter $d_{50}$ value of the surface-treated calcium carbonate is in the range between 0.1 µm to 250 µm, preferably between 1 µm and 200 µm, more preferably between 1 µm and 150 µm, even more preferably between 1 µm and 100 µm and most preferably between 3 µm and 100 µm, measured according to the sedimentation method. For example, the surface-treated calcium carbonate has a weight median particle diameter $d_{50}$ value of 19.5 µm. Alternatively, the surface-treated calcium carbonate has a weight median particle diameter $d_{50}$ value of 1.4 µm. A surface-treated calcium carbonate having a $d_{98}$ of less than 100 microns, preferably of less than 85 microns may also be advantageous, for example 83 microns. Alternatively, surface-treated calcium carbonate having a $d_{98}$ of less than 20 microns, preferably of less than 10 microns may be advantageous, for example 5 microns.

The inventive surface-treated calcium carbonate preferably has a specific surface area of from 0.5 m$^2$/g to 120 m$^2$/g, preferably 0.5 m$^2$/g to 100 m$^2$/g and more preferably 0.5 m$^2$/g to 75 m$^2$/g, measured using nitrogen and the BET method. For example, the surface-treated calcium carbonate has a specific surface area of from 0.5 m$^2$/g to 10 m$^2$/g, e.g. a specific surface area of 0.61 m$^2$/g. Alternatively, the surface-treated calcium carbonate has a specific surface area of from 5 m$^2$/g to 15 m$^2$/g, e.g. a specific surface area of 5.5 m$^2$/g.

In one preferred embodiment, the surface-treated calcium carbonate further comprises at least one microorganism capable of degrading at least one component of the hydrocarbon-containing composition.

For the purposes of the present invention, microorganism which "degrade" at least one component of the hydrocarbon-containing composition correspond to microorganisms having the ability to convert at least one component of the hydrocarbon-containing composition into inactive forms and/or smaller molecules, e.g. by utilizing these substrates as intermediates in their pathways.

If the surface-treated calcium carbonate further comprises at least one microorganism capable of degrading at least one component of the hydrocarbon-containing composition, said surface-treated calcium carbonate and said at least one microorganism may be in the separated form and/or said surface-treated calcium carbonate is immobilized with said at least one microorganism.

If the surface-treated calcium carbonate and the at least one microorganism capable of degrading at least one component of the hydrocarbon-containing composition are in the separated form, both the surface-treated calcium carbonate and the at least one microorganism are preferably in the form of a suspension. Such suspensions can be present in accordance with well-known forms and can be prepared by methods well known to the skilled person.

For example, the inventive surface-treated calcium carbonate is present in powder form and/or in the form of granules and the at least one microorganism capable of degrading at least one component of the hydrocarbon-containing composition is present in the form of an aqueous suspension. Alternatively, the inventive surface-treated calcium carbonate is present in the form of slurry and the at least one microorganism capable of degrading at least one component of the hydrocarbon-containing composition is present in the form of an aqueous suspension. Optionally, the aqueous suspension of the at least one microorganism capable of degrading at least one component of the hydrocarbon-containing composition further comprises nutrients such as phosphate, ammonium nitrate, proteins, alkali metal ammonium phosphates, glucose, dextrose, urea, yeast and the like. Additionally or alternatively, these nutrients may be present in the slurry of said surface-treated calcium carbonate.

In one especially preferred embodiment, the surface-treated calcium carbonate is immobilized with at least one microorganism capable of degrading at least one component of the hydrocarbon-containing composition.

In general, the surface-treated calcium carbonate is immobilized with the at least one microorganism in accordance with well-known methods. For example, an immobilization method can be used which comprises the exposure of surface-treated calcium carbonate to an aqueous suspension of the at least one microorganism to be immobilized. If desired, such exposure can be only for a time sufficient to permit adsorption of the microorganism onto the surface-treated calcium carbonate. Alternatively, if the aqueous suspension comprises a nutrient broth, such exposure can be for a longer period of time which will permit some growth of microorganism during the immobilization procedure on the surface-treated calcium carbonate. Additionally or alternatively, the immobilization method may comprise confining the microorganism to the pores of the surface-treated calcium carbonate under reduced pressure.

In this regard, no particular restriction is put on the microorganism to be utilized with the surface-treated calcium carbonate of the present invention, but suitable microorganisms are selected from microorganisms known to have a degrading ability to various hydrocarbons usually found in crude oil and/or a refined petroleum product. Examples of microorganisms capable of degrading at least one component of the hydrocarbon-containing composition which may be suitably used in the present invention are selected from the group comprising at least one strain of bacteria and/or fungi.

In one preferred embodiment, the at least one strain of bacteria and/or fungi capable of degrading at least one component of the hydrocarbon-containing composition is at least one strain of petroleum-degrading bacteria and/or petroleum-degrading fungi.

In one preferred embodiment, the at least one strain of bacteria and/or fungi capable of degrading at least one component of the hydrocarbon-containing composition is at least one strain of petroleum-degrading bacteria or petroleum-degrading fungi. Alternatively, the at least one strain of bacteria and/or fungi capable of degrading at least one component of the hydrocarbon-containing composition is at least one strain of petroleum-degrading bacteria and petroleum-degrading fungi.

Specific examples of strains of bacteria which may be suitably used in the present invention are selected from the group comprising *Psychrobacter, Pseudomonas, Pseudobacterium, Acinetobacter, Vibrio, Planococcus, Actinobacterium, Arthrobacter, Marinobacter, Methylosinus, Methylomonas, Methylobacterium, Mycobacterium, Nocardia, Bacillus, Brevibacterium, Micrococcus, Corynebacterium, Sarcina, Streptomyces, Flavobacterium, Xanthomonas* and mixtures thereof.

In one especially preferred embodiment, the at least one strain of bacteria is selected from the group comprising *Psychrobacter glacincola, Acinetobacter calcoaceticus, Acinetobacter faecalis* and mixtures thereof.

In one preferred embodiment, the at least one strain of bacteria capable of degrading at least one component of the hydrogen-containing composition is at least one strain of genetically modified bacteria, i.e. the bacteria have been genetically engineered in order to upregulate the metabolic pathway for degrading at least one component of the hydrocarbon-containing composition.

In one preferred embodiment, the at least one strain of fungi capable of degrading at least one component of the hydrocarbon-containing composition is at least one strain of filamentous fungi.

Specific examples of strains of fungi which may be suitably used in the present invention are selected from the group comprising *Aspergillus flavus, Aspergillus fumigates, Aspergillus niger, Aspergillus niveus, Aspergillus terreus, Aspergillus versicolor, Fusarium* sp., *Mortierella* spp., *Mucor, Mycelia, Penicillium corylophilum, Paecilomyces niveus, Paecilomyces variotti, Rhizopus, Talamoryces, Trichoderma* spp. and mixtures thereof.

In one preferred embodiment, the at least one microorganism capable of degrading at least one component of the hydrocarbon-containing composition is a microorganism that is capable of degrading at least two components of the hydrocarbon-containing composition, preferably at least three components of the hydrocarbon-containing composition and most preferably a plurality of components of the hydrocarbon-containing composition.

The at least one microorganism capable of degrading at least one component of the hydrocarbon-containing composition is selected such that the at least one microorganism shows a degradation rate for the hydrocarbon-containing composition of at least 25%, preferably of at least 40%, more preferably of at least 50%, even more preferably of at least 60% and most preferably of at least 70%, based on the total weight of the hydrocarbon-containing composition. In one especially preferred embodiment, the at least one microorganism capable of degrading at least one component of the hydrocarbon-containing composition shows a degradation rate for the hydrocarbon-containing composition of at least 75%, based on the total weight of the hydrocarbon-containing composition.

In one preferred embodiment, the at least one microorganism capable of degrading at least one component of the hydrocarbon-containing composition is a mixture of at least two microorganisms capable of degrading at least one component of the hydrocarbon-containing composition. Preferably, the at least one microorganism capable of degrading at least one component of the hydrocarbon-containing composition is a mixture of at least three microorganisms capable of degrading at least one component of the hydrocarbon-containing composition. Preferably, if the at least one microorganism capable of degrading at least one component of the hydrocarbon-containing composition is a mixture of at least two microorganisms, one microorganism is a bacterial strain of *Psychrobacter glacincola*.

The inventive surface-treated calcium carbonate can be present in any appropriate form, e.g. in the form of granules or a powder or in the form of a cake. Preferably, the surface-treated calcium carbonate is in powder form and/or in the form of granules. In a preferred embodiment, the surface-treated calcium carbonate is in powder form. Alternatively, the surface-treated calcium carbonate can be present as an aqueous suspension, e.g. in the form of slurry.

A "slurry" or "suspension" in the meaning of the present invention comprises insoluble solids, i.e. surface-treated calcium carbonate and water and optionally further additives. Suspensions usually contain large amounts of solids and are more viscous and generally of higher density than the liquid from which they are formed. It is accepted in the art that the general term "dispersion" inter alia covers "suspensions" or "slurries" as a specific type of dispersion.

In one preferred embodiment, the inventive surface-treated calcium carbonate is suspended in water such that the slurry has a content of surface-treated calcium carbonate within the range of 1 wt.-% to 80 wt.-%, more preferably 3 wt.-% to 60 wt.-%, and even more preferably 5 wt.-% to 40 wt.-%, based on the weight of the slurry.

The surface-treated calcium carbonate can be kept in suspension, optionally further stabilised by a dispersant. Conventional dispersants known to the skilled person can be used. A preferred dispersant is polyacrylic acid.

Within the context of the present invention, it is also possible to provide a nonwoven fabric comprising the inventive surface-treated calcium carbonate. In this regard, conventional nonwoven fabrics known to the skilled person can be used. For example, nonwoven fabrics can be used that are manufactured by forming a fiber layer (fiber web) by means of a dry method, a wet process, or the like, and bonding fibers in the fiber layer to each other by means of a chemical bonding method, a thermal bonding method, or the like.

In one preferred embodiment, the inventive surface-treated calcium carbonate is incorporated in a biodegradable nonwoven fabric. If the nonwoven fabric is biodegradable, the nonwoven fabric is preferably made of cotton, flax, hemp, jute, ramie, coir, sisal, abaca, kenaf, bagasse or mixtures thereof. For example, the biodegradable nonwoven fabric is made of cotton and/or flax. It is preferred that the biodegradable nonwoven fabric is made of cotton or flax.

In one preferred embodiment, the nonwoven fabric comprises the inventive surface-treated calcium carbonate immobilized with at least one microorganism capable of degrading at least one component of the hydrocarbon-containing composition. Optionally, the nonwoven fabric may further comprise nutrients as described above.

In another preferred embodiment, the nonwoven fabric comprises the inventive surface-treated calcium carbonate and an aqueous suspension of at least one microorganism capable of degrading at least one component of the hydrocarbon-containing composition, optionally the aqueous suspension of the at least one microorganism further comprises nutrients as described above.

In accordance with the present invention, the surface-treated calcium carbonate is suitable for effectively binding and bioremediating hydrocarbon-containing compositions and has a degradation rate for the hydrocarbon-containing composition of at least 25%, based on the total weight of the hydrocarbon-containing composition.

In one preferred embodiment, the surface-treated calcium carbonate is selected such that a degradation rate for the hydrocarbon-containing composition of at least 40%, preferably of at least 50%, more preferably of at least 60% and most preferably of at least 70%, based on the total weight of the hydrocarbon-containing composition, is obtained. In one especially preferred embodiment, the surface-treated calcium carbonate is selected such that a degradation rate for the hydrocarbon-containing composition of at least 75%, based on the total weight of the hydrocarbon-containing composition, is obtained.

A "hydrocarbon-containing composition" as used herein refers to a composition comprising at least one hydrocarbon, i.e. the composition comprises at least one type of hydrocarbons. In one preferred embodiment, the hydrocarbon-containing composition comprises at least two hydrocarbons, i.e. the composition comprises at least two types of hydrocarbons. In an especially preferred embodiment, the hydrocarbon-containing composition comprises a plurality of hydrocarbons, i.e. the composition is a mixture of different types of hydrocarbons.

Examples of hydrocarbons include aliphatic hydrocarbons, aromatic hydrocarbons, nitro-aromatic hydrocarbons, halo-aliphatic hydrocarbons, halo-aromatic hydrocarbons and mixtures thereof. In one preferred embodiment, the hydrocarbon-containing composition comprises at least one type of hydrocarbons selected from the group comprising alkanes such as methane, ethane, propane, butane, isobutane, pentane, isopentane, neopentane, hexane, heptane, 2,4-dimethylhepane, octane, isooctane, nonane, decane, undecane, dodecane, tridecane, tetradecane, pentadecane, hexadecane, heptadecane, octadecane, nonadecane and eicosane and mixtures thereof; alkenes such as ethene, propene, butene, butadiene, isobutene, pentene, hexene, heptene, octene, nonene, and decene and mixtures thereof; alkynes such as ethyne, propyne, butyne, pentyne, hexyne, heptyne, octyne, nonyne, and decyne and mixtures thereof; cycloalkanes such as cyclopropane, cyclobutane, methylcyclopropane, cyclopentane, methylcyclopentane, cyclohexane, cycloheptane, methylcyclohexane, cyclooctane, cyclononane and cyclodecane and mixtures thereof; alkadienes such as allene, butadiene, pentadiene, isoprene, hexadiene, heptadiene, octadiene, nonadiene, decadiene and mixtures thereof and aromatic hydrocarbons such as benzene, naphthalene, anthracene, acenaphthene, acenaphthylene, benzopyrene, pyrene, toluene, xylenes, trimethylbenzene, ethylbenzene, methylnaphthalene, aniline, phenol, phenanthrene and dimethylphenol and mixtures thereof.

The exact chemical composition of crude oil and refined petroleum products varies depending on the origin of the crude oil.

In one preferred embodiment, the hydrocarbon-containing composition comprises from 10 wt.-% to 90 wt.-% of one type of hydrocarbon, preferably from 15 wt.-% to 75 wt.-%, more preferably from 20 wt.-% to 65 wt.-%, even more preferably from 25 wt.-% to 65 wt.-% and most preferably from 30 wt.-% to 65 wt.-%, based on the total weight of the hydrocarbon-containing composition.

In a further preferred embodiment, the hydrocarbon-containing composition comprises two or more types of hydrocarbons with each hydrocarbon present in a certain amount. In one especially preferred embodiment, a first type of hydrocarbon is present in an amount from 1 wt.-% to 25 wt.-% and a second type of hydrocarbon is present in amount from 70 wt.-% to 90 wt.-% based on the total weight of the hydrocarbon-containing composition. In another preferred embodiment, a first type of hydrocarbon is present in an amount from 10 wt.-% to 50 wt.-% and a second type of hydrocarbon is present in amount from 40 wt.-% to 80 wt.-% based on the total weight of the hydrocarbon-containing composition. In a further preferred embodiment, a first type of hydrocarbon is present in an amount from 20 wt.-% to 60 wt.-% and a second type of hydrocarbon is present in amount from 30 wt.-% to 75 wt.-% based on the total weight of the hydrocarbon-containing composition.

In one especially preferred embodiment, a mixture of four to six types of hydrocarbons is present in an amount of at least 40 wt.-%, more preferably of at least 50 wt. % and most preferably of at least 60 wt.-%, based on the total weight of the hydrocarbon-containing composition. For example, a mixture of five types of hydrocarbons is present in an amount of at least 40 wt.-%, more preferably of at least 50 wt. % and most preferably of at least 60 wt.-%, based on the total weight of the hydrocarbon-containing composition.

In one preferred embodiment, the hydrocarbon-containing composition is crude oil and/or a refined petroleum product selected from the group comprising gasoline, diesel fuel, aviation fuel, hydraulic oil, kerosene and mixtures thereof.

In accordance with another aspect of the present invention, the method for binding and bioremediating hydrocarbon-containing compositions comprises a step of providing a hydrocarbon-containing composition. Another step of the present method comprises the provision of at least one inventive surface-treated calcium carbonate, wherein at least 10% of the aliphatic carboxylic acid accessible surface area of the calcium carbonate is covered by a coating comprising at least one aliphatic carboxylic acid having between 5 and 24 carbon atoms and/or reaction products thereof. A further step of the inventive method comprises contacting the hydrocarbon-containing composition with the at least one surface-treated calcium carbonate for obtaining a composite material of surface-treated calcium carbonate and hydrocarbon-containing composition.

In one preferred embodiment, the hydrocarbon-containing composition is crude oil and/or a refined petroleum product selected from the group comprising gasoline, diesel fuel, aviation fuel, hydraulic oil, kerosene and mixtures thereof.

In another preferred embodiment, the step of contacting the hydrocarbon-containing composition with the at least one surface-treated calcium carbonate wherein at least 10% of the aliphatic carboxylic acid accessible surface area of the calcium carbonate is covered by a coating comprising at least one aliphatic carboxylic acid having between 5 and 24 carbon atoms and/or reaction products thereof preferably takes place in that the surface of the hydrocarbon-containing composition is at least partially covered with the at least one surface-treated calcium carbonate. Additionally or alternatively, the step of contacting the hydrocarbon-containing composition with the at least one surface-treated calcium carbonate preferably takes place in that the hydrocarbon-containing composition of step a) is mixed with the surface-treated calcium carbonate of step b). The skilled man will adapt the mixing conditions (such as the configuration of mixing speed) according to his needs and available equipment.

In one especially preferred embodiment, the surface-treated calcium carbonate is incorporated in a nonwoven fabric which may be placed on the surface of the hydrocarbon-containing composition. In one preferred embodiment, the nonwoven fabric is a biodegradable nonwoven fabric.

In one further preferred embodiment, the surface-treated calcium carbonate is immobilized with at least one microorganism capable of degrading at least one component of the hydrocarbon-containing composition.

The treatment time for carrying out the contacting of the at least one hydrocarbon-containing composition with the at least one surface-treated calcium carbonate is carried out for a period of 5 min or more, preferably for a period of 1 hour or more, more preferably for a period of 12 hours or more and most preferably for a period of 24 hours or more. In general, the length of contacting the hydrocarbon-containing composition with the at least one surface-treated calcium carbonate is determined by the degree of hydrocarbon-pollution and the medium to be treated. For example, where the degree of hydrocarbon-pollution is restricted to spatially confined areas such as a leak of hydraulic oil on sealed concrete, the treatment time is as short as, for example, 5 minutes to 6 hours. If the degree of hydrocarbon-pollution is of a huge extent such as a hydrocarbon pollution of sea water and the corresponding shore line affected by an oil spill, the treatment time can be as long as, for example, about 12 hours to 90 days. In one preferred embodiment, the treatment time is about 60 to 90 days.

It is to be understood that the amount of surface-treated calcium carbonate according to the present invention is selected such that it is sufficient in the hydrocarbon-containing composition, i.e. high enough for providing efficient binding and bioremediating activity for at least one type of hydrocarbon present in the hydrocarbon-containing composition but at the same time is so low that no significant amount of unbound surface-treated calcium carbonate would be observed on the polluted medium to treated. In other words, by using the inventive surface-treated calcium carbonate or method efficient binding and bioremediating activity is provided and huge (and thus unwanted) amounts of surface-treated calcium carbonate are avoided.

In one preferred embodiment, the contacting of the at least one hydrocarbon-containing composition with the at least one surface-treated calcium carbonate is carried out in that the weight ratio of hydrocarbon-containing composition and surface-treated calcium carbonate is from 10:1 to 1:100, more preferably from 1:1 to 1:50, even more preferably from 1:1 to 1:25 and most preferably from 1:1 to 1:15.

In one preferred embodiment, the method further comprises the step of contacting the composite material obtained in step c) with a composition comprising at least one microorganism capable of degrading at least one component of the hydrocarbon-containing composition.

If the composite material of surface-treated calcium carbonate and hydrocarbon-containing composition is further contacted with a composition comprising at least one microorganism capable of degrading at least one component of the hydrocarbon-containing composition, said composition may be provided in any appropriate form known to the skilled person.

For example, the composition comprising at least one microorganism capable of degrading at least one component of the hydrocarbon-containing composition of step d) may be provided in the form of an aqueous suspension. If the at least one microorganism is at least one strain of bacteria, the bacteria density of the aqueous suspension to be added to the polluted medium to be treated depends on the concentration of hydrocarbon-containing composition posed on the polluted medium. In one preferred embodiment, the bacteria density of the aqueous suspension is in the range of 1 cells/Liter to $10^8$ cells/Liter, more preferably in the range of $10^2$ cells/Liter to $10^6$ cells/Liter and most preferably in the range of $10^4$ cells/Liter to $10^5$ cells/Liter.

Such aqueous suspension comprising microorganisms may be sprayed onto the surface of the composite material of surface-treated calcium carbonate and hydrocarbon-containing composition and/or may be injected into the polluted medium that comprises the composite material of surface-treated calcium carbonate and hydrocarbon-containing composition by suitable pumping means. Depending on the selected at least one microorganism capable of degrading at least one component of the hydrocarbon-containing composition, the growth of the microorganism added to the polluted medium may be supported by also spraying and/or injecting sufficient amounts of key nutrients such as phosphate, ammonium nitrate, proteins, alkali metal ammonium phosphates, glucose, dextrose, urea, yeast and the like. Such nutrients may be added to the aqueous suspension comprising the microorganism. Additionally or alternatively, said nutrients may be injected into and/or sprayed onto the surface of the composite material in a separate aqueous suspension.

In case the surface-treated calcium carbonate is incorporated in a nonwoven fabric, said nonwoven fabric can be further treated with said aqueous suspension comprising microorganisms in that the aqueous suspension is sprayed onto the nonwoven fabric and/or injected into the nonwoven fabric. Optionally, nutrients may be sprayed onto the nonwoven fabric and/or injected into the nonwoven fabric as described above.

In one preferred embodiment of the present invention, the composition comprising at least one microorganism capable of degrading at least one component of the hydrocarbon-containing composition is added to the composite material of surface-treated calcium carbonate and hydrocarbon-containing composition in an amount of from 1 ppm to 10.000 ppm, preferably in amount of from 250 ppm to 5.000 ppm and most preferably is in the range of 500 ppm to 2.500 ppm, calculated relative to the hydrocarbon-containing composition.

The ratios of the surface-treated calcium carbonate and the composition comprising at least one microorganism capable of degrading at least one component of the hydrocarbon-containing composition may vary over a wide range. In the composite material according to the invention, the ratio of the surface-treated calcium carbonate and the microorganism composition corresponds preferably to a weight ratio of from 10:1 to 1:10, preferably from 5:1 to 1:5, particularly preferably from 2:1 to 1:2.

The composition comprising at least one microorganism capable of degrading at least one component of the hydrocarbon-containing composition preferably comprises aerobic bacteria. If water is to be treated with the composition comprising at least one microorganism capable of degrading at least one component of the hydrocarbon-containing composition, the oxygen content in the water is preferably at least 0.2 mg/Liter, more preferably at least 0.5 mg/Liter, even more preferably at least 1 mg/Liter and most preferably at least 1.5 mg/Liter.

Examples of strains of bacteria which may be suitably utilized in step d) of the present method are selected from the group comprising *Psychrobacter, Pseudomonas, Pseudobacterium, Acinetobacter, Vibrio, Planococcus, Actinobacterium, Arthrobacter, Marinobacter, Methylosinus, Methylomonas, Methylobacterium, Mycobacterium, Nocardia, Bacillus, Brevibacterium, Micrococcus, Corynebacterium, Sarcina, Streptomyces, Flavobacterium, Xanthomonas* and mixtures thereof.

In one especially preferred embodiment, the composition comprising at least one microorganism capable of degrading at least one component of the hydrocarbon-containing composition comprises a bacterial strain selected from the group comprising *Psychrobacter glacincola, Acinetobacter calcoaceticus, Acinetobacter faecalis* and mixtures thereof.

Examples of strains of fungi which may be suitably utilized in step d) of the present method are selected from the group comprising *Aspergillus flavus, Aspergillus fumigates, Aspergillus niger, Aspergillus niveus, Aspergillus terreus, Aspergillus versicolor, Fusarium* sp., *Mortierella* spp., *Mucor, Mycelia, Penicillium corylophilum, Paecilomyces niveus, Paecilomyces variotti, Rhizopus, Talamoryces, Trichoderma* spp. and mixtures thereof.

The composition comprising at least one microorganism capable of degrading at least one component of the hydrocarbon-containing composition as utilized in step d) of the inventive method is preferably selected such that the at least one microorganism shows a degradation rate for the hydrocarbon-containing composition of at least 25%, preferably of at least 40%, more preferably of at least 50%, even more preferably of at least 60% and most preferably of at least 70%, based on the total weight of the hydrocarbon-containing composition. In one especially preferred embodiment, the composition comprising at least one microorganism capable of degrading at least one component of the hydrocarbon-containing composition utilized in step d) of the inventive method shows a degradation rate for the hydrocarbon-containing composition of at least 75%, based on the total weight of the hydrocarbon-containing composition.

In one preferred embodiment, the composition comprising at least one microorganism capable of degrading at least one component of the hydrocarbon-containing composition comprises a mixture of at least two microorganisms capable of degrading at least one component of the hydrocarbon-containing composition. Preferably, the composition comprising at least one microorganism capable of degrading at least one component of the hydrocarbon-containing composition comprises a mixture of at least three microorganisms capable of degrading at least one component of the hydrocarbon-containing composition. Even more preferably, the composition comprising at least one microorganism capable of degrading at least one component of the hydrocarbon-containing composition comprises a plurality of microorganisms capable of degrading at least one component of the hydrocarbon-containing composition. If the composition comprising at least one microorganism capable of degrading at least one component of the hydrocarbon-containing composition comprises a mixture of at least two microorganisms, one microorganism is preferably a bacterial strain of *Psychrobacter glacincola*.

In one especially preferred embodiment, the surface-treated calcium carbonate of step b) is further immobilized with at least one microorganism capable of degrading at least one component of the hydrocarbon-containing composition.

In one preferred embodiment, step c) and step d) are carried out simultaneously. If step c) and step d) are carried out simultaneously, the inventive surface-treated calcium carbonate and the composition comprising at least one microorganism capable of degrading at least one component of the hydrocarbon-containing composition are preferably provided together in the form of slurry, i.e. the slurry comprises the inventive surface-treated calcium carbonate as well as the composition comprising at least one microorganism capable of degrading at least one component of the hydrocarbon-containing composition.

Alternatively, step c) and step d) are carried out separately. In this case, the hydrocarbon-containing composition is first contacted with the surface-treated calcium carbonate and then with the composition comprising at least one microorganism capable of degrading at least one component of the hydrocarbon-containing composition In one preferred embodiment of the inventive method, step c) or step d) is repeated one or more times. In a further preferred embodiment, step c) and step d) are repeated one or more times. If step c) and step d) are repeated one or more times, step c) and step d) may be repeated independently, i.e.

step c) may be repeated several times, while step d) is repeated more or less times than step c) and vice versa. For example, step c) may be repeated twice, while step d) is repeated once or more than twice.

The use of the inventive surface-treated calcium carbonate or method for binding hydrocarbon-containing compositions provides a number of improved properties. First of all, the inventive surface-treated calcium carbonate provides excellent binding and bioremediating activity when at least partially applied onto the surface of a hydrocarbon-containing composition or mixed with the hydrocarbon-containing composition. Furthermore, the inventive surface-treated calcium carbonate provides excellent binding and bioremediating activity when at least partially applied onto the surface of a hydrocarbon-containing composition and mixed with the hydrocarbon-containing composition. Furthermore, the inventive surface-treated calcium carbonate provides excellent binding and bioremediating activity when incorporated in a nonwoven fabric, for example, a biodegradable nonwoven fabric and applied onto the surface of a hydrocarbon-containing composition in the form of said nonwoven fabric. Preferably, the inventive surface-treated calcium carbonate provides excellent binding and bioremediating activity when applied onto the surface of a hydrocarbon-containing composition if the inventive surface-treated calcium carbonate further comprises an aqueous suspension of at least one microorganism capable of degrading at least one component of the hydrocarbon-containing composition and/or is immobilized with at least one microorganism capable of degrading at least one component of the hydrocarbon-containing composition.

The addition or the use of the inventive surface-treated calcium carbonate or method results in a composite material of surface-treated calcium carbonate and hydrocarbon-containing composition which can be easily removed from the polluted medium to be treated. Furthermore, the binding and bioremediating of hydrocarbon-containing compositions by the inventive surface-treated calcium carbonate results in a good cleansing quality of the medium to be treated.

The surface-treated calcium carbonate may be stored for indefinitely long periods, is not categorized as toxic product and can be easily spread over the polluted medium to be treated. Furthermore, the surface-treated calcium carbonate further comprising an aqueous suspension of at least one microorganism capable of degrading at least one component of the hydrocarbon-containing composition and/or is immobilized with at least one microorganism capable of degrading at least one component of the hydrocarbon-containing composition permit an efficient binding of the hydrocarbon-containing composition as well as an efficient bioremediation of the hydrocarbon-containing composition within a short period of time.

Depending on the specific requirements and/or the respective physical and/or chemical properties of the hydrocarbon-containing composition to be treated, the surface-treated calcium carbonate and the composition comprising at least one microorganism capable of degrading at least one component of the hydrocarbon-containing composition to be used according to the inventive method can be applied both separately or a finished mixture may be used. In the form of a separately metered addition of the individual components of the surface-treated calcium carbonate and the composition comprising at least one microorganism capable of degrading at least one component of the hydrocarbon-containing composition the concentration ratio may be individually adjusted depending on the present polluted medium to be treated. The polluted medium may be treated with the surface-treated calcium carbonate being formulated, for example, as a customary formulation, such as, for example, a solution, an emulsion, a suspension, a powder, a foam, pastes, granules, aerosols and incorporations in nonwoven fabrics.

A further advantage of the inventive surface-treated calcium carbonate or the inventive method resides in the fact that the used surface-treated calcium carbonate accelerates a biological remediation process of the hydrocarbon-containing composition without disturbing the ecological balance. Another advantage of the inventive surface-treated calcium carbonate or the inventive method is that none of the employed components, namely the surface-treated calcium carbonate and/or the at least one microorganism capable of degrading at least one component of the hydrocarbon-containing composition, give rise to subsequent pollution of the medium to be treated.

Among applications in soils, shore lines, sea water, flat water or ground water, the most important application is the cleansing of hydrocarbon-containing compositions distributed accidentally. In particular, oil spills affected by releases of crude oil from tankers, offshore platforms, drilling rigs and wells, as well as spills of refined petroleum products and heavier fuels used by large ships such as bunker fuel, or the spill of oily refuse or waste oil are considered as important applications. Applications may also be possible for cleansing of hydrocarbon-polluted media originated in different industries such as railroad, airline and land transport industries as well as the oil storage, transportation, refining and fuel-dispensing industries. In this regard, the cleansing of containers, reservoirs and all kind of means for storing, transporting, refining and fuel-dispensing are considered as important applications.

In view of the very good results of the surface-treated calcium carbonate in binding and bioremediating of hydrocarbon-containing compositions from polluted media as defined above, a further aspect of the present invention is the use thereof for binding and bioremediating hydrocarbon-containing compositions. According to another aspect of the present invention, a composite material comprising the surface-treated calcium carbonate and a hydrocarbon-containing composition is provided. With regard to the definition of the surface-treated calcium carbonate and/or the hydrocarbon-containing composition and preferred embodiments thereof, reference is made to the statements provided above when discussing the technical details of the surface-treated calcium carbonate and/or the hydrocarbon-containing composition.

The following examples may additionally illustrate the invention, but are not meant to restrict the invention to the exemplified embodiments. The examples below show the good microbiological stability of the aqueous preparations of minerals, pigments or fillers protected with the composition according to the present invention:

EXAMPLES

Measurement Methods

The following measurement methods were used to evaluate the parameters given in the examples and claims.

BET Specific Surface Area of a Material

The BET specific surface area was measured via the BET method according to ISO 9277 using nitrogen, following conditioning of the sample by heating at 250° C. for a period of 30 minutes. Prior to such measurements, the sample was filtered, rinsed and dried at 110° C. in an oven for at least 12 hours.

Particle Size Distribution (Mass % Particles with a Diameter<X) and Weight Median Diameter ($d_{50}$) of a Particulate Material Weight median grain diameter and grain diameter mass distribution of a particulate material were determined via the sedimentation method, i.e. an analysis of sedimentation behaviour in a gravitational field. The measurement was made with a Sedigraph™ 5100.

The method and the instrument are known to the skilled person and are commonly used to determine grain size of fillers and pigments. The measurement was carried out in an aqueous solution of 0.1 wt.-% $Na_4P_2O_7$. The samples were dispersed using a high speed stirrer and ultrasound.

Aerobic Degradation

Measurements were carried out in accordance with the OECD 301 D close bottle test.

Anaerobic Degradation

Measurements were carried out in accordance with the OECD 311.

Anaerobic biodegradability of organic compounds in digested sludge was carried out by measurement of gas production.

Biological Oxygen Demand

BOD was assessed as described in OECD 301D.

Analytical GC-MS

Samples were extracted with diethyl ether and analysed on an AutoSystem XL Perkin Elmer according to the standard method of the RDS-ANA lab (Report 58072.10)

Aliphatic Carboxylic Acid Accessible Surface Area

The aliphatic carboxylic acid accessible surface area may be determined by the method described in the publication of Papier, Schultz and Turchi (Eur. Polym. J., Vol. 20, No. 12, pp. 1155-1158, 1984).

Example 1

The following illustrative Example involves the use of a surface-treated natural calcium carbonate powder for binding and bioremediating a hydrocarbon-containing composition by determining the residual hydrocarbon compounds over a period of 60 days for aerobic and anaerobic samples, respectively. Said surface-treated natural calcium carbonate powder has a weight medium particle diameter $d_{50}$ value of 1.4 μm (measured according to the sedimentation method) and a specific surface area of 5.5 $m^2/g$ (measured using nitrogen and the BET method), before surface treatment. The surface-treated natural calcium carbonate is covered by a coating comprising stearic acid and/or reaction products thereof. Stearic acid and/or reaction products of stearic acid are present in the coating in an amount of 0.7 wt.-%, based on the dry weight of the calcium carbonate.

Aerobic and anaerobic biodegradation of crude oil in seawater were performed with seawater sampled from a fjord close to the Omya molde in Norway. 1000 ppm crude oil was used and the sinking agent was the surface-treated natural calcium carbonate powder as described above. The surface-treated natural calcium carbonate was used in a weight ratio of surface-treated calcium carbonate and hydrocarbon-containing composition of 10:1. The biogas (BG) production were monitored over a period of 60 days at 10° C. for the aerobic and anaerobic samples respectively. The residual hydrocarbon compounds were measured by GC-MS. Table 1 summaries the details of the utilized strains of bacteria and the measured oil recovery.

TABLE 1

| Sample | Condition | Bacteria | Oil recovery (%; GC-MS) |
| --- | --- | --- | --- |
| Sea water-oil | aerobic | no | 100 |
| Sea water-oil | aerobic | activated sludge | 60 |
| Sea water-oil | aerobic | Ultra-microbes | 65 |
| Sea water-oil | anaerobic | no | 100 |
| Sea water-oil | anaerobic | digested sludge | 77 |
| Sea water-oil | anaerobic | *Psychrobacter glacincola* | 100 |

The Ultra-Microbes bacteria were provided by UltraTech (USA) and are the oldest registered biological/microbial product on the EPA's National Contingency Products List for water applications involving oil. The sludge samples were sampled from a plant in Aarburg. The GC-MS profiles provide an indication of the bioremediated oil compared to the control samples without microorganisms. During the aerobic degradation in the presence of activated sludge and Ultra-Microbes as well as in the anaerobic sample inoculated with the digested sludge a reduction of about 30% of the hydrocarbons was measured by GC-MS. It can thus be concluded that during the aerobic degradation a bacteria oil-degrading activity is given.

Example 2

The following illustrative Example involves the use of a surface-treated natural calcium carbonate powder (cf. Example 1 above) for binding and bioremediating a hydrocarbon-containing composition in sea water by determining the residual hydrocarbon compounds over a period of 60 days at a temperature of about 4° C.

Aerobic bioremediation of 100 ppm petroleum in seawater was performed at 4° C. during a period of time of 60 days. The surface-treated natural calcium carbonate was used in a weight ratio of surface-treated calcium carbonate and hydrocarbon-containing composition of 10:1. The residual hydrocarbon compounds were measured by GC-MS. Table 2 summaries the details of the utilized bacteria and the measured oil recovery.

TABLE 2

| Sample | Bacteria | Oil recovery (%; GC-MS) |
| --- | --- | --- |
| Sea water-oil | no | 100 |
| Sea water-oil | *Psychrobacter glacincola* | 22 |
| Sea water-oil | activated sludge | 60 |
| Sea water-oil | digested sludge | 65 |
| Sea water-oil | seafloor sludge | 87 |
| Sea water-oil | Ultra-microbes | 100 |

During the aerobic bioremediation, a bioremediation of about 78% to 13% was obtained at 4° C. depending on the microorganism utilized. The combination of surface-treated calcium carbonate and bacterial species *Psychrobacter glacincola*, a hydrocarbon-degrading bacterial strain isolated from extremely cold habitats, achieved a bioremediation of up to 78% compared to the initial hydrocarbon concentration as determined by GC-MS. Using the sewage samples from different plants, a bioremediation of about 35% and 40% was obtained. In contrast, the microorganisms of the seafloor sludge bioremediated only about 13% of the hydrocarbons and the Ultra-microbes did not show any bioremediation activity at 4° C. It can thus be concluded that during binding and the aerobic bioremediation a bacteria oil-degrading activity is given.

Example 3

The following illustrative Example involves the use of a surface-treated natural calcium carbonate powder (cf. Example 1 above) in combination with the commercially available dispersing agent Corexit 9500 (commercially available from Nalco, USA) for binding and bioremediating a hydrocarbon-containing composition in sea water by determining the residual hydrocarbon compounds over a period of 60 days at a temperature of about 4° C. Furthermore, the residual hydrocarbon compounds over a period of 60 days at a temperature of about 4° C. for the surface-treated natural calcium carbonate powder/Corexit 9500 combination are compared with results obtained for the surface-treated natural calcium carbonate powder.

Aerobic bioremediation of crude oil in seawater was performed with seawater containing a dispersant. 100 ppm petroleum was used and the sinking agent was the surface-treated natural calcium carbonate powder as described above in combination with the commercially available dispersing agent Corexit 9500 (Nalco). The surface-treated natural calcium carbonate was used in a weight ratio of surface-treated calcium carbonate and hydrocarbon-containing composition of 10:1. The residual hydrocarbon compounds were measured by GC-MS. Table 3 summaries the details of the utilized bacteria and the measured oil recovery.

TABLE 3

| Sample | Bacteria | Oil recovery (%; GC-MS) |
|---|---|---|
| Sea water-oil | no | 100 |
| Sea water-oil | *Psychrobacter glacincola* | 66 |
| Sea water-oil | activated and digested sludge | 47 |
| Sea water-oil | seafloor sludge molde 1 | 69 |
| Sea water-oil | seafloor sludge molde 2 | 100 |
| Sea water-oil | Ultra-microbes | 100 |

The following table 4 outlines the oil recovery for the surface-treated natural calcium carbonate powder/Corexit 9500 combination in comparison with the results obtained for the surface-treated natural calcium carbonate powder over a period of 60 days at a temperature of about 4° C.

TABLE 4

| Sample | Bacteria | Oil recovery (%; GC-MS) No dispersant | Oil recovery (%; GC-MS) Dispersant COREXIT 9500 |
|---|---|---|---|
| Sea water-oil | no | 100 | 100 |
| Sea water-oil | *Psychrobacter glacincola* | 22 | 66 |
| Sea water-oil | activated and digested sludge | 62 | 47 |
| Sea water-oil | seafloor sludge molde 1 | 87[a] | 69 |
| Sea water-oil | seafloor sludge molde 2 | | 100 |
| Sea water-oil | Ultra-microbes | 100 | 100 |

[a] A mixture (1:1) of both seafloor samples

Example 4

Determination of Viability of Bacteria after Immobilization on $CaCO_3$

*Pseudomonas* sp. and *Psychobacter glacinola* were immobilized on $CaCO_3$ and stored for 31 days at room temperature. After storage the bacterial viability was determined.

Portions of 100 μl (>$10^9$ CFU/ml PBS) of a suspension of *Pseudomonas* sp. and *Psychobacter glacinola* were each mixed separately with 100 μl of sterile PBS, 80% sterile glycerol, edible oil (rapeseed oil), and polyethylene glycol (Fluka order number 82280), which served as solvents for the microorganisms.

Natural ground calcium carbonate was coated with stearic acid in amounts of 0.2 wt %, 0.6 wt % and 1.2 wt %. The BET specific surface area was 0.61 $m^2/g$ and the weight median size was 19.5 μm.

Each suspension of the 200 μl premixed bacteria was mixed with 4 g of the stearic acid coated calcium carbonate samples. The samples were vortexed during 1 minute and agitated during 30 minutes on a Turbula-mixer and incubated at room temperature in closed vials. After 3, 10, and 31 days, 1 g of the dry calcium carbonate powder with immobilized bacteria was used for the determination of TVC (Total Viable Counts).

For this determination 1 g of powder was mixed with 9 ml of disruption buffer (10 mM Tris buffered in 0.9% saline, pH 8.0) in order to detach the microorganisms from the white pigment powder samples. The suspensions are shaken on a vortex for 60 sec. at 2500 rpm before being put on the rotation shaker for 30 minutes at 400 UpM (at room temperature).

From these preparations 100 μl samples were plated on a TSA plate (Tryptic-Soy-Agar) and incubated up to 5 days at 30° C. Without saying, all operations must be made under sterile conditions.

All quoted bacterial counts (Total Viable Count (TVC) values are in cfu/ml) in the Tables herebelow are determined after 5 days following plate-out and in accordance with counting method described in "Bestimmung von aeroben mesophilen Keimen", Schweizerisches Lebensmittelbuch, chapter 56, section 7.01, edition of 1985, revised version of 1988.

Table 5 to 7 list the results with *Pseudomonas* sp., table 8 lists the results for *Psychobacter glacinola*

TABLE 5

TVC results obtained with a culture of *Pseudomonas* (after 3 days of storage at room temperature).

| solvent for microorganisms | stearic coating on $CaCO_3$ | TVC |
|---|---|---|
| 80% glycerol | 1.2% | <100 |
| | 0.6% | <100 |
| | 0.2% | <100 |
| edible oil | 1.2% | >>$10^4$ |
| | 0.6% | >>$10^4$ |
| | 0.2% | >>$10^4$ |
| polyethylene glycol | 1.2% | <100 |
| | 0.6% | <100 |
| | 0.2% | <100 |
| water/PBS | 1.2% | >>$10^4$ |
| | 0.6% | >>$10^4$ |
| | 0.2% | >>$10^4$ |

TABLE 6

TVC results obtained with a culture of *Pseudomonas* (after 10 days of storage at room temperature).

| solvent for microorganisms | stearic coating on $CaCO_3$ | TVC |
|---|---|---|
| 80% glycerol | 1.2% | <100 |
| | 0.6% | <100 |
| | 0.2% | <100 |

TABLE 6-continued

TVC results obtained with a culture of *Pseudomonas* (after 10 days of storage at room temperature).

| solvent for microorganisms | stearic coating on CaCO$_3$ | TVC |
|---|---|---|
| edible oil | 1.2% | >>10$^4$ |
| | 0.6% | >>10$^4$ |
| | 0.2% | >>10$^4$ |
| polyethylene glycol | 1.2% | <100 |
| | 0.6% | <100 |
| | 0.2% | <100 |
| water/PBS | 1.2% | 3.2 * 10$^4$ |
| | 0.6% | >>10$^4$ |
| | 0.2% | >>10$^4$ |

TABLE 7

TVC results obtained with a culture of *Pseudomonas* (after 31 days of storage at room temperature).

| solvent for microorganisms | stearic coating on CaCO$_3$ | TVC |
|---|---|---|
| 80% glycerol | 1.2% | <100 |
| | 0.6% | <100 |
| | 0.2% | <100 |
| edible oil | 1.2% | >>10$^4$ |
| | 0.6% | >>10$^4$ |
| | 0.2% | >>10$^4$ |
| polyethylene glycol | 1.2% | <100 |
| | 0.6% | <100 |
| | 0.2% | <100 |
| Water/PBS | 1.2% | >>10$^4$ |
| | 0.6% | 3.5 * 10$^4$ |
| | 0.2% | 3.18 * 10$^4$ |

Disruption buffer: <10, as negative control

Growth of colonies was judged after 24 and 48 hours (after 3 days [table 5] only after 24 hours since *Pseudomonas* is a fast growing species). The results after 48 hours were the same as after 24 hours.

TABLE 8

TVC results obtained with a culture of *Psychrobacter* (after 21 days of storage at room temperature. Plates were judged at different days, plating of bacteria occurred once).

| solvent for microorganisms | stearic coating on CaCO$_3$ | TVC 48 h | TVC 72 h | TVC 7 days |
|---|---|---|---|---|
| 80% glycerol | 1.2% | <100 | <100 | 2.8 * 10$^3$ |
| | 0.6% | <100 | <100 | <100 |
| | 0.2% | <100 | <100 | <100 |
| edible oil | 1.2% | sc | >>10$^4$ | >>10$^4$ |
| | 0.6% | sc | >10$^4$ | >>10$^4$ |
| | 0.2% | sc | >10$^4$ | >>10$^4$ |
| polyethylene glycol | 1.2% | <100 | <100 | <100 |
| | 0.6% | <100 | <100 | <100 |
| | 0.2% | <100 | <100 | <100 |
| Water/PBS | 1.2% | sc | >10$^4$ | 10$^4$ |
| | 0.6% | sc | 1.7 * 10$^3$ | 4.7 * 10$^3$ |
| | 0.2% | sc | 10$^4$ | >10$^4$ |

Disruption buffer: <10 (3 and 7 days) as negative control

Edible oil: <10 after 1 and 5 days of incubation of the TSA. Since the edible oil was neither sterilized, nor micro-filtered, a negative control was necessary to exclude that possible bacteria growth was due to present microorganisms in the edible oil due to contamination.

The results nicely show that microorganisms when immobilized on treated calcium carbonate can be stored for at least 31 day without loss of growing power, particularly in both edible oil and water/PBS.

Overall, it can be concluded that the use of the dispersing agent COREXIT 9500 in combination with a surface-treated calcium carbonate has no positive effect on the binding and bioremediation efficiency of the bacterial strain *Psychrobacter glacincola* which showed a bioremediation of up to 34% of petroleum (compared to the initial hydrocarbon concentration as determined by GC-MS). In contrast thereto, the inventive surface-treated calcium carbonate achieves a bioremediation of up to 78% compared to the initial hydrocarbon concentration as determined by GC-MS. In this context, it should be noted that the dispersing agent COREXIT 9500 used in combination with the surface-treated calcium carbonate also contains several organic compounds. Thus, it has to be assumed that the excess of oil foreign organic compounds might have an impact on the metabolic balance of the utilized bacterial strains and thus on the bioremediation of the respective petroleum compounds.

The invention claimed is:

1. A method for binding and bioremediating a hydrocarbon-containing composition that has polluted or contaminated an environmental medium, comprising contacting the hydrocarbon-containing composition in the environmental medium with a surface-treated calcium carbonate and with, simultaneously or separately, a composition comprising at least one microorganism capable of degrading at least one component of the hydrocarbon-containing composition, to bind and bioremediate the hydrocarbon-containing composition in the environmental medium, wherein the surface-treated calcium carbonate is calcium carbonate treated with at least one aliphatic carboxylic acid having between 5 and 24 carbon atoms such that at least 10% of the aliphatic carboxylic acid accessible surface area of the calcium carbonate is covered by a coating comprising the aliphatic carboxylic acid and/or reaction products thereof, wherein the hydrocarbon-containing composition in the environmental medium is selected from the group consisting of crude oil, a refined petroleum product, gasoline, diesel fuel, aviation fuel, hydraulic oil, kerosene, and any mixture thereof, and wherein the environmental medium is soil, sea water, ground water, flat water, a shore line, or a reservoir.

2. The method according to claim 1, wherein the contacting is carried out by at least partially covering a surface of the hydrocarbon-containing composition with the surface-treated calcium carbonate or mixing the hydrocarbon-containing composition with the surface-treated calcium carbonate.

3. The method according to claim 1, which results in a degradation rate of at least 25% for the hydrogen-containing composition.

4. The method according to claim 1, wherein the weight ratio of hydrocarbon-containing composition and surface-treated calcium carbonate is from 10:1 to 1:100.

5. The method according to claim 1, wherein the weight ratio of hydrocarbon-containing composition and surface-treated calcium carbonate is from 1:1 to 1:50.

6. The method according to claim 1, wherein the at least one microorganism capable of degrading at least one component of the hydrocarbon-containing composition is at least one strain of bacteria and/or fungi.

7. The method according to claim 1, wherein the at least one microorganism capable of degrading at least one component of the hydrocarbon-containing composition is at least one strain of petroleum-degrading bacteria and/or petroleum-degrading fungi.

8. The method according to claim 1, wherein the at least one microorganism capable of degrading at least one component of the hydrocarbon-containing composition is selected from the group consisting of *Psychrobacter, Pseudomonas, Pseudobacterium, Acinetobacter, Vibrio, Planococcus, Actinobacterium, Arthrobacter, Marinobacter, Methylosinus, Methylomonas, Methylobacterium, Mycobacterium, Nocardia, Bacillus, Brevibacterium, Micrococcus, Corynebacterium, Sarcina, Streptomyces, Flavobacterium, Xanthomonas* and any mixture thereof.

9. The method according to claim 1, wherein the at least one microorganism capable of degrading at least one component of the hydrocarbon-containing composition is selected from the group consisting of *Psychrobacter glacincola, Acinetobacter calcoaceticus, Acinetobacter faecalis* and any mixture thereof.

10. The method according to claim 1, wherein the calcium carbonate comprises ground calcium carbonate, precipitated calcium carbonate, surface-modified calcium carbonate, or any mixture thereof.

11. The method according to claim 1, wherein the calcium carbonate is ground calcium carbonate.

12. The method according to claim 11, wherein the ground calcium carbonate is obtained from marble, chalk, calcite, dolomite, limestone and any mixture thereof.

13. The method according to claim 1, wherein the surface-treated calcium carbonate has a weight median particle diameter $d_{50}$ value of between 0.1 μm and 250 μm.

14. The method according to claim 1, wherein the surface-treated calcium carbonate has a weight median particle diameter $d_{50}$ value of between 0.1 μm and 100 μm.

15. The method according to claim 1, wherein the coating of the surface-treated calcium carbonate comprises at least one aliphatic carboxylic acid selected from the group consisting of pentanoic acid, hexanoic acid, heptanoic acid, octanoic acid, nonanoic acid, decanoic acid, undecanoic acid, lauric acid, tridecanoic acid, myristic acid, pentadecanoic acid, palmitic acid, heptadecanoic acid, stearic acid, nonadecanoic acid, arachidic acid, heneicosylic acid, behenic acid, tricosylic acid, lignoceric acid and any mixture thereof.

16. The method according to claim 1, wherein the coating of the surface-treated calcium carbonate comprises at least one aliphatic carboxylic acid selected from the group consisting of octanoic acid, decanoic acid, lauric acid, myristic acid, palmitic acid, stearic acid, arachidic acid and any mixture thereof.

17. The method according to claim 1, wherein the coating of the surface-treated calcium carbonate comprises at least one aliphatic carboxylic acid selected from the group consisting of myristic acid, palmitic acid, stearic acid and any mixture thereof.

18. The method according to claim 1, wherein at least 20% of the aliphatic carboxylic acid accessible surface area of the calcium carbonate is covered by a coating comprising the aliphatic carboxylic acid and/or reaction products thereof.

19. The method according to claim 1, wherein at least 50% of the aliphatic carboxylic acid accessible surface area of the calcium carbonate is covered by a coating comprising the aliphatic carboxylic acid and/or reaction products thereof.

20. The method according to claim 1, wherein the surface-treated calcium carbonate comprises the at least one microorganism capable of degrading at least one component of the hydrocarbon-containing composition.

21. The method according to claim 1, wherein the surface-treated calcium carbonate is immobilized with the at least one microorganism capable of degrading at least one component of the hydrocarbon-containing composition.

22. The method according to claim 1, wherein the surface-treated calcium carbonate is in powder form and/or in the form of granules or in the form of slurry.

23. The method according to claim 1, wherein the surface-treated calcium carbonate is incorporated in a nonwoven fabric.

24. The method according to claim 1, wherein the surface-treated calcium carbonate is incorporated in a biodegradable nonwoven fabric.

25. The method according to claim 1, wherein the environmental medium is sea water, flat water, or a shore line.

26. The method according to claim 1, wherein the environmental medium is sea water and the hydrocarbon-containing composition is crude oil or a refined petroleum product from a tanker.

27. The method according to claim 1, wherein the environmental medium is sea water and the hydrocarbon-containing composition is crude oil from a tanker, an offshore platform or a drilling rig.

28. The method according to claim 1, wherein the environmental medium is soil.

29. A composition for binding and bioremediating a hydrocarbon-containing composition that has polluted or contaminated an environmental medium, wherein the composition comprises (i) at least one microorganism capable of degrading at least one component of the hydrocarbon-containing composition selected from the group consisting of crude oil, a refined petroleum product, gasoline, diesel fuel, aviation fuel, hydraulic oil, kerosene, and any mixture thereof, and (ii) a surface-treated calcium carbonate, wherein the surface-treated calcium carbonate is calcium carbonate treated with at least one aliphatic carboxylic acid having between 5 and 24 carbon atoms such that at least 10% of the aliphatic carboxylic acid accessible surface area of the calcium carbonate is covered by a coating comprising the aliphatic carboxylic acid and/or reaction products thereof.

30. The composition according to claim 29, wherein the surface-treated calcium carbonate is immobilized with the at least one microorganism.

31. The composition according to claim 29, wherein the at least one strain of microorganism is selected from the group consisting of *Psychrobacter, Pseudomonas, Pseudobacterium, Acinetobacter, Vibrio, Planococcus, Actinobacterium, Arthrobacter, Marinobacter, Methylosinus, Methylomonas, Methylobacterium, Mycobacterium, Nocardia, Bacillus, Brevibacterium, Micrococcus, Corynebacterium, Sarcina, Streptomyces, Flavobacterium, Xanthomonas* and any mixture thereof.

32. The composition according to claim 29, wherein the calcium carbonate comprises ground calcium carbonate, precipitated calcium carbonate, surface-modified calcium carbonate, or any mixture thereof.

33. The composition according to claim 29, wherein the surface-treated calcium carbonate is incorporated in a nonwoven fabric.

34. The composition according to claim 29, wherein the surface-treated calcium carbonate is incorporated in a biodegradable nonwoven fabric.

* * * * *